United States Patent [19]

Gonzalez

[11] Patent Number: 5,783,686
[45] Date of Patent: Jul. 21, 1998

[54] METHOD FOR PURIFYING NUCLEIC ACIDS FROM HETEROGENOUS MIXTURES

[75] Inventor: Diana Gonzalez, Placentia, Calif.

[73] Assignee: Beckman Instruments, Inc., Fullerton, Calif.

[21] Appl. No.: 529,148

[22] Filed: Sep. 15, 1995

[51] Int. Cl.$^6$ .................................................. C07H 1/00
[52] U.S. Cl. ............... 536/25.4; 536/25.41; 536/25.42; 536/127; 435/803; 423/335
[58] Field of Search .......................... 536/25.4, 25.41, 536/25.42, 127; 423/335; 435/803

[56] References Cited

U.S. PATENT DOCUMENTS

| | | |
|---|---|---|
| 4,923,978 | 5/1990 | McCormich . |
| 5,057,426 | 10/1991 | Henco et al. . |
| 5,075,430 | 12/1991 | Little . |
| 5,155,018 | 10/1992 | Gillespie et al. . |
| 5,204,257 | 4/1993 | DeBonville et al. . |
| 5,273,718 | 12/1993 | Sköld et al. . |

FOREIGN PATENT DOCUMENTS

| | | |
|---|---|---|
| 0 281 390 | 9/1988 | European Pat. Off. . |
| 0 512 767 A1 | 11/1992 | European Pat. Off. . |
| 0 512 768 A1 | 11/1992 | European Pat. Off. . |
| 0 580 305 A2 | 1/1994 | European Pat. Off. . |
| WO 89/01035 | 2/1989 | WIPO . |
| WO 93/11218 | 6/1993 | WIPO . |
| WO 93/11221 | 6/1993 | WIPO . |

*Primary Examiner*—James O. Wilson
*Attorney, Agent, or Firm*—William H. May; P. R. Harder; Fulbright & Jaworski

[57] ABSTRACT

Discloses DNA isolation and purification methods which involve novel washing steps. The disclosed methods provide a means for isolating and purifying DNA from a homogeneous mixture of DNA of other cellular contaminants by treating silica with the homogeneous mixture containing DNA in the presence of a chaotropic salt solution and then washing and separating the washed and treated silica in successive wash steps with aqueous alcohol wash solutions. A first wash step involves washing the treated silica with a first wash solution of at least 95 wt % alcohol in water. A second wash step similarly involves washing the treated and washed silica with second wash solution of less than 95 wt % alcohol in water.

16 Claims, No Drawings

METHOD FOR PURIFYING NUCLEIC ACIDS FROM HETEROGENOUS MIXTURES

BACKGROUND OF THE INVENTION

1. Field of the Invention

The present invention relates generally to isolating and purifying DNA from heterogenous mixtures containing DNA and other materials. More particularly, the present invention relates to methods and reagents for obtaining high purity DNA using readily available buffers, solvents and materials. Advantageously, the present invention is adaptable for use on automated laboratory instrumentation and provides DNA having a purity sufficiently high for use in the most demanding applications including automated fluorescent cycle DNA sequencers.

2. Description of Relevant Art

Rapid advancements in molecular biology have placed a great deal of emphasis on the ability to isolate and purify DNA from a variety of different sources. Depending upon its source, DNA will be present in mixtures along with a variety of other components including proteins, lipids, and other cellular materials. The ability to isolate DNA from these mixtures and subsequently purify the isolated DNA is important in many methodologies including recombinant DNA studies and techniques, genetic studies, and molecular diagnostics. In particular, as the use of automated fluorescent cycle sequencers increases, high throughput methods for providing highly purified DNA have become desirable. Sources of DNA include cleared bacterial or yeast lysates containing plasmid or cosmid DNA or other vectors, blood or urine containing genomic DNA, recombinant phage lysates, DNA amplification reactions, and other systems used in molecular biological methods.

In recent years a number of isolation and purification methods have been reported and commercialized. Early methods relied upon performing extended centrifugation steps or two phase extractions using aqueous phenol or chloroform plus ethanol precipitation and wash steps. These techniques are time consuming, and can require expensive instrumentation and costly and noxious reagents. Moreover, extraction and precipitation techniques are difficult to automate since one phase must be pipetted to remove it from the other. Chromatographic techniques, particularly high pressure liquid chromatography and column chromatography, have been used successfully for shorter chain nucleic acids. However, longer chain nucleic acids frequently experience chain scission from excessive mechanical agitation.

Recently commercialized purification systems rely upon the ability of DNA to bind to the surface of glass and/or silicates, such as diatomaceous earth preparations or glass beads. These systems provide glass or silicate slurries for isolating DNA from heterogeneous mixtures and solutions such as low ionic strength buffers and organic solvents, for subsequently washing the immobilized DNA and silica and then eluting the DNA from the surface of the glass or silicate. A common disadvantage associated with these systems is that the isolated DNA is not sufficiently pure for many particularly demanding procedures such as automated fluorescent cycle DNA sequencing and subsequent amplification reactions. Thus, further purification of the eluted and recovered DNA is required, which in turn adds additional time and expense to the purification process. Additionally, because it can require the use of chromatographic columns and precipitation and resuspension steps, further purification is not adaptable for use in connection with common laboratory automation instrumentation.

Other methodologies for isolating DNA from mixtures have been suggested in recent years. For example U.S. Pat. No. 5,057,426 suggests separating DNA from mixtures containing DNA by fixing the DNA onto an anion exchange resin and removing the resin from the mixture by filtration. To recover the fixed DNA from the resin, the DNA is differentially eluted using salts or other ionic systems which compete for sites on the anion exchange resin.

In a different approach, U.S. Pat. No. 4,923,978 suggests treating a solid material such as glass beads or silica so that its surface is coated with a hydrophilic material. These surfaces are said to selectively bind proteinaceous materials and not DNA. Thus, DNA can be isolated by allowing DNA and protein containing mixtures to come into contact with the treated solid material and subsequently removing the treated material, leaving behind isolated DNA which is suspended or in solution.

European Patent Application No. 0 512 767 A1 suggests using up to 100% ethyl alcohol as a binding agent to replace chaotropes typically used to facilitate binding DNA to the surface of solid particles such as silica. This process is characterized as requiring further purification subsequent to removing DNA from the surface of the solid particles for use in automated fluorescent cycle sequencing.

Characteristic of most bacterial plasmid purification methodologies is an alkaline lysis procedure, followed by treatment with silica in the presence of a chaotrope and then a wash step and an elution step. In order to obtain DNA suitable for automated fluorescent cycle DNA sequencing applications, these methods require further purification which can include column filtration or a reprecipitation followed by another wash and a resuspension of the purified DNA. It is generally recognized that these multiple step purification processes are labor intensive.

Furthermore, with the recent emphasis on laboratory automation there is increased interest in DNA purification methods which are easily adaptable to robotic systems. The popular silica based isolation and purification systems currently in use which require further purification after washing the silica are not suitable for robotic system.

Accordingly, it is an object of the present invention to provide methods for isolating and recovering plasmid DNA which is sufficiently pure for automated fluorescent cycle sequencing applications without the need for post wash precipitation and washes.

It is another object of the present invention to provide plasmid DNA purification methods which are easily adaptable to automated laboratory systems.

It is a further object of the present invention to provide DNA purification methods which do not require expensive equipment and reagents.

SUMMARY OF THE INVENTION

The present invention satisfies the above-identified objectives by providing DNA isolation and purification methods which involve novel washing steps. More particularly, the methods of the present invention provide a means for isolating and purifying DNA from a homogeneous mixture by treating silica with the homogeneous mixture containing DNA in the presence of a chaotropic salt solution and then washing the treated silica in successive wash steps with aqueous alcohol wash solutions. A first wash step involves washing the treated silica with a first wash solution of at least 95 wt % alcohol in water. A second wash step similarly involves washing the treated and washed silica with second wash solution of less than 95 wt % alcohol in water.

Subsequent to each wash step, the used wash solution is separated from the washed silica in order to remove unwanted material and impurities from the wash system.

When washing silica exposed to mixtures containing DNA in accordance with the teachings of the present invention, the treated and washed silica contains DNA which is sufficiently pure for use in automated fluorescent cycle sequencing methodologies. In order to recover the isolated and purified DNA from the surface of the silica for subsequent uses, the silica is simply washed with water or water in combination with low ionic strength buffers. This causes the DNA to elute from the silica into the water wash. After separating the solution containing the eluted DNA from the silica, the purified DNA is ready for use.

In preferred embodiments of the present invention the first and second wash solutions are about 95–99 wt % ethyl alcohol in water and about 70–85 wt % ethyl alcohol in water, respectively. Most preferred first and second wash solution are about 99 wt % ethyl alcohol in water and 75 wt % ethyl alcohol in water, respectively. However, depending upon the source of DNA, one skilled in the art is credited with optimizing the amount of alcohol —between 95–99 wt % for the first wash and between 70–85 wt % for the second wash. Additionally, as those skilled in the art will recognize, separating the used wash solution from the washed silica preferentially involves filtering the silica through appropriately sized filters subsequent to each wash step. This provides for removing unwanted impurities which have been removed from the silica following each wash step.

The novel wash steps of the present invention are effective in providing an environment for DNA to remain bound to the silica while removing substantially all proteinaceous materials, lipids, unwanted cellular debris, and the chaotropic salts used in first exposing the DNA mixture to silica. Subsequently eluting the isolated DNA from the silica provides sufficiently pure DNA which requires no further purification steps such as solvent precipitation and subsequent washes or spin column purification. Accordingly, the present invention provides simple time-saving methods using conventional materials and inexpensive equipment. Alternatively, the simplicity of the present invention allows for the complete automation of the DNA isolation and purification process using, for example, robotic laboratory equipment.

Additional advantages associated with the methods of the present invention will be recognized by those skilled in the art upon an understanding of the invention as described in the following detailed description.

DETAILED DESCRIPTION OF THE INVENTION

The present invention is based upon the discovery that when silica based DNA purification methods utilize successive wash steps of very highly concentrated aqueous alcohol solution followed by a significantly less concentrated aqueous alcohol solution, DNA elutes from the silica and has significantly increased purity. The present invention is unlike prior art methods which incorporate one wash step, utilize wash solutions having a significant salt concentration and require post wash reprecipitations to remove excessive salt. Advantageously, the present invention does not require post elution purification such as solvent reprecipitation and spin column elutions.

Broadly, the present invention involves methods for isolating DNA from a homogeneous mixture of DNA and other material and includes first treating silica with the homogeneous mixture and a chaotrope and then successively washing the treated silica with first and second wash solutions, respectively. The first wash solution is at least 95 wt % alcohol in water and the second wash solution is less than 95 wt % alcohol in water. The present invention further provides for separating wash solution from the washed silica, subsequent to each of the first and second wash steps. This assures that the excess chaotrope and unbound cellular material are removed after treating the silica. The successive wash steps and separation steps, when performed in connection with first treating silica with the DNA mixture in the presence of a chaotrope solution, provide pure DNA isolated on the surface of the silica.

In preferred embodiments each wash step is repeated twice and further includes mixing the treated silica with the appropriate wash solution, incubating the mixture of treated silica and wash solution followed by filtering the incubated mixture through an appropriately sized filter. In accordance with the present invention and in order to recover purified DNA, the washed, filtered, and dried silica containing isolated DNA is eluted with water or a low ionic strength buffer.

DNA from any source can be purified in accordance with the methods of the present invention. Those skilled in the art are familiar with the many materials and process mixtures which are routinely subjected to DNA purification procedures. Typical sources include a) clinical samples such as blood, urine, semen etc. b) genomic libraries; c) PCR or other amplification reaction systems; d) bacterial lysates; and e) viruses. Molecular biologists are most commonly concerned with recovering plasmids from bacteria for the purpose of cloning and/or sequencing DNA. For this reason, the present invention is described in terms of isolating and recovering purified plasmid from bacterial sources. Those skilled in the art will recognize, however, that the present invention is applicable to any source of DNA.

As will be described below, preferred embodiments of the present invention involve the use of a first wash solution of about 99 wt % ethyl alcohol in water and a second wash solution of about 75 wt % ethyl alcohol in water. However, first aqueous based wash solutions which have more than 95 wt % alcohol apparently provide an environment for the DNA to remain bound to the silica while removing competing impurities. The second aqueous based wash solution provides a greater amount of water (less than 95 wt % alcohol) and effectively removes the remainder of the impurities while the isolated DNA remains bound to the surface of the silica. In general, it has been determined that if the amount of water in the first wash step is less than 95 wt % alcohol the yield of DNA is reduced and purity is improved. Similarly, if 100 wt % alcohol is utilized in the first wash solution the yield is improved but the resulting DNA contains substantial impurities.

As already mentioned a typical method of the present invention involves the recovery of purified plasmid from a bacterial lysate. Accordingly, typical purification procedures first require the preparation of the bacterial lysate from a bacterial culture. Those skilled in the art are credited with being familiar with methods for lysing bacteria. The present invention is described in terms of the known alkaline lysis Birnboim procedure (Birnboim & Doly, 1979, and Birnboim, 1982), however, any procedure which effectively lysis the bacterial cells and releases DNA is applicable. Typically these procedures involve adding a bacterial pellet to solutions which break open the bacterial cells, and cause the bacterial chromosomes, cell membranes and other components to form a precipitate while leaving the plasmid DNA in solution.

Accordingly, for a small scale plasmid purification procedure using bacteria which has been transformed with a plasmid containing a DNA sequence of interest, a 1–2 mL sample of bacterial culture is centrifuged in a plate-well format so that the bacteria settle into a pellet at the bottom of the wells. Then the plate is inverted to drain the liquid. A solution of 50 mM glucose, 25 mM Tris pH 8 buffer, 10 mM EDTA at pH8 and 100–1000 μg/mL RNAse A (concentration depends upon RNAse A activity) is added to the pellet. This is followed by adding a solution of 0.2 N NaOH and 1 wt % SDS which lysis the bacteria and denatures the bacterial proteins and the chromosomal and plasmid DNA. Finally, adding a third solution of 3 M potassium acetate at pH 5 neutralizes the mixture and causes the covalently closed plasmid to reanneal. The chromosomal DNA, proteins and high molecular weight RNA aggregate into a solid mass. The cell lysate obtained from the above described procedure is then separated from the precipitate by passing the lysate through a filter which retains the contaminating precipitate and allows the lysate containing the plasmid DNA to flow through.

Filters suitable for separating the lysate from the precipitate are low protein binding with a sufficiently small pore size, typically 3 μm or less. In higher throughput procedures which take advantage of 96 well technologies, a preferred filter is in the form of a 96 well filter plate available from PALL Corp. East Hills N.Y. and sold under the Trademarks of Loprodyne/Loprosorb. This is a two layer filter membrane system with the top layer being a tightly woven fibrous mesh and the bottom layer being a 3 μm pore size nylon membrane. Those skilled in the art will recognize that an alternative method for separating the lysate from the precipitate is a centrifugation step. Typical centrifuging methods involve about 5 minutes at around 2500 rpm.

In accordance with the present invention a suitable amount of silica is treated with the bacterial lysate obtained as the filtrate in the above-described lysis procedure in the presence of a solution containing a high concentration of a chaotropic salt. Silica from a variety of sources is suitable in the practice of the present invention and can include glass beads and diatomaceous earth. The particle size of the silica is not crucial and can range from sub-micron diameters to over 100 μm in diameter. In preferred embodiments the silica has an average particle size of between 5 μm and 10 μm.

Preferably the silica is an hydroxylated having enriched surface hydroxyl functionalities. Such hydroxylated silica is available from Beckman Instruments of Fullerton, Calif. and is sold under the trademark Ultrasphere.

Chaotropic agents are known in the art and have found recent use in DNA purification systems. In the presence of high concentrations of a chaotropic agent DNA will selectively bind to silica. Apparently the chaotropic agent reduces the interaction of water molecules with the DNA so that the DNA preferentially hydrogen bonds with the surface of the silica rather than remaining in the aqueous solution. Any chaotropic agent is useful in the practice of the present invention including but not limited to guanidine thiocyanate, sodium iodide, sodium perchlorate, and guanidine hydrochloride. Preferred embodiments of the present invention use aqueous solutions of 6 M guanidine hydrochloride. Best results are achieved when the chaotropic agent is present in relatively high concentrations ranging from 5 M to 7 M.

In accordance with the present invention after the DNA is allowed to interact with the silica in the presence of the chaotropic agent, the treated silica is separated from the aqueous mixture. A variety of methods can be used to remove the treated silica including allowing the aqueous mixture to drain from the silica while the silica is packed in a funnel type arrangement. In preferred embodiments, the combination of treated silica and aqueous mixture is passed through a filter membrane. The membrane traps the treated silica with the deposited DNA and allows the chaotropic agent and some impurities from the lysate to pass in the filtrate. At this point the treated silica also contains small amounts of proteinaceous material, and other bacterial cell components which must be removed in order to obtain sufficiently pure DNA.

The next step in the present DNA purification method involves washing the treated silica with a first wash solution of aqueous alcohol which is preferably greater than 95 wt % in water and most preferably about 99 wt % in water. The wash procedure involves mixing the treated silica with the wash solution, incubating the resulting mixture and then separating the filtrate from the treated and wash silica. Preferably the separating is accomplished by filtering the washed silica, however, centrifugation is an alternative separation technique. The wash, incubation, and separation process preferably is repeated at least once and most preferably twice.

A final wash process involves washing the treated, washed and filtered silica in a manner similar to that used in the first wash step, except that the second wash solution is less than 95 wt % alcohol. Most preferably, the second wash solution is about 75 wt % ethyl alcohol. This second wash step is mixed and incubated for a few minutes to allow for any residual chaotropic agent and other contaminates such as proteinaceous material to go into solution. Finally, the washed silica is separated from the filtrate by filtering through a suitable filter or by centrifugation. For optimum results, the second wash step is repeated at least once and most preferably twice, and the final filtering is performed until the silica is dry.

Alcohols suitable in the practice of the present invention are low molecular weight and water soluble including but not limited to methyl alcohol, ethyl alcohol, and isopropyl alcohol. In preferred embodiments the alcohol is ethyl alcohol, however, the purity and yield of DNA treated in accordance with the present invention are good using any of the lower alkyl alcohols.

Filters suitable for separating the alcohol wash solutions from the treated and washed silica include most filters having appropriate pore sizes for retaining the silica. As mentioned above, an advantage of the present invention is its adaptability to 96 well plate format and automation. In embodiments which adopt this format a particularly preferred filter is a 96 well filter plate available from PALL Corp. and sold under the trademark Loprodyne. The filter portion of the plate is a low protein binding nylon having a 3 μm pore size.

The result of the two wash steps described above is an isolated DNA deposited on the surface of the silica, the unwanted cellular impurities and excess chaotropic agents having been removed in the wash filtrates. In order to recover the purified DNA for subsequent use the DNA is eluted from the silica in a procedure which is similar to the wash step, except that the DNA is present in the eluting solution. Water is the preferred eluting medium and provides the greatest advantages for DNA which is to be used in DNA sequencing applications. Advantageously, because water is a particularly suitable eluting medium, the resulting DNA is salt free. Unlike prior art purification procedures which typically include salts in their wash solutions. DNA purified in accordance with the present invention is substantially salt free. As will be demonstrated in the examples which follow, when sequencing such salt free DNA a significantly reduced number of sequencing errors occur. Those skilled in the art will recognize however, that low salt concentration buffers typical of those known in the art for handling DNA can be utilized as an eluting medium as well.

The following examples are offered in order to illustrate the embodiments of the present invention and are not to be taken as limiting the invention.

Example 1

The following experiment was performed using a 96 well format, the bacterial cultures, cell lysing, washing and eluting having taken place in suitable 96 well plates. This experiment describes a typical cell lysing and DNA purification procedure in accordance with the present invention.

Bacterial Culture Preparation

To obtain the bacteria for lysing, 2 mLs of culture median containing ampicillin to 50 µg/mL were placed in small test tubes. Each tube was inoculated with a sterile toothpick touched with a colony of interest. The E. coli strains used were αDH5 and XL1 transformed with pBluescript or pUC based plasmids. The cultures were grown aerobically and once grown can be processed or frozen for future processing. The cultures were transferred to a square well plate (from Beckman Instruments, Fullerton, Calif.) and centrifuged at about 2500 RPM for 5 minutes to pellet the bacteria and inverted to drain the liquid. The plates were then loaded on a Biomek automated laboratory workstation (Beckman Instruments, Fullerton, Calif.). The Biomek was programmed for automated processing in accordance with the general directions provided with the instrument.

Bacterial Lysate Preparation

An aqueous buffer and stabilizing solution was prepared having the following components: 50 mM glucose, 25 mM Tris HCL at pH 8, 10 mM EDTA, 850 µg/mL RNAseA. All of the components were purchased from Sigma Chemicals of St. Louis, Mo. with the exception of the RNAseA which was purchased from Biodyne. An aqueous lysing solution was prepared having the following components: 0.2 N NaOH and 1 wt % SDS, both components purchased from JT Baker. Finally, a third aqueous solution of 3 M potassium (from JT Baker) acetate at pH5 was prepared.

The following steps are described in terms of the individual operation performed by the Biomek, but can be performed using manual pipetting and transfer procedures. In order to lyse the bacterial cells, 100 µL of the stabilizing buffer solution and 200 µL of the lysing solution were added to each well containing the bacterial pellet. The wells were allowed to incubate at room temperature for 5 minutes. Finally, 150 µL of the third solution was added to each well to neutralize the mixture and cause the plasmid DNA to preferentially reanneal and remain in solution while the chromosomal DNA and protein SDS complexes aggregate into a gummy mass.

The mixture in each well was filtered through a Loprodyne/Loprosorb filter plate using vacuum to pull the clear lysate through to another corresponding set of wells in a 96 well plate. The gummy mass was retained in the filter plate.

Bacterial Lysate DNA Purification

To each well of clear bacterial lysate, 175 µL of hydroxylated silica slurry (17 wt % silica) was added. The hydroxylated silica is known as Ultrashpere and is a 10 µm particle size. Also added to each well was aqueous 6 M guanidine hydrochloride (purchased from JT Baker) solution. The mixture of lysate, silica, and guanidine hydrochloride solution was mixed and allowed to sit for 5 minutes. The liquid in each of the 96 wells was passed then through a 96 well filter plate (Loprodyne) which does not allow the silica to pass.

The novel washing steps of the present invention were performed as follows: To the silica in each of the wells, 200 µL of an aqueous 99 wt % ethyl alcohol was added. The content of the wells was mixed and incubated about 5 minutes and then the wash solution was filtered off using a vacuum filtration techniques. The filter used was a Loprodyne plate filter. This wash procedure was repeated. Next, 200 µL of an aqueous 75 wt % ethyl alcohol solution was added to each well containing the silica. The content of each well was mixed, incubated 5 minutes and filtered as just described for the first washing step. This second washing process was repeated twice. Finally, the silica was exposed to vacuum filtration until dry.

In order to recover the isolated DNA in a pure form, 70 µL of water was added to each of the wells containing the washed silica. The 96 well plate was incubated for about 5 minutes. A collection plate was placed under the filter plate and the silica was filtered, collecting the water containing pure plasmid. The yield of pure DNA is at least 1 µg/mL of starting culture.

Example 2

Since DNA purity is a factor in the success of DNA sequencing methods, automated fluorescent cycle DNA sequencing experiments were conducted to demonstrate the superior purity of DNA purified in accordance with the present invention. The discussion and experiments described below show that DNA purified in accordance with the present invention can be used in automated sequencing without further purification and provide exceptional results when compared with commercially available systems.

Bacterial lysate prepared as described above was subjected to two commercially available DNA purification procedures and a DNA purification process in accordance with the present invention. More particularly, DNA purification kits purchased from Promega and Qiagen were used to prepare plasmid for automated fluorescent cycle sequencing on a ABI instrument according to manufacturer's instructions. The Bacterial lysate for these experiments was prepared as described in Example 1, above and the lysate purification was performed in accordance with the procedures recommended by the purification kit manufacturer. Additionally, purified plasmid DNA prepared as described in Example 1 was subjected to automated sequencing on the same instrument. The plasmids which were sequenced were pBluescript (pBlue) transformed in αDH5 and XL1, respectively. Table I provides the sequencing data in the form of the number of sequencing errors in the sequencing run for a 350 base sequence, a 400 base sequence, 450 base sequence and 500 base sequence, respectively. Sequencing ambiguities rather than absolute errors are indicated with a (±) in Table I.

TABLE I

| Purification Process | Plasmid | No. Bases | | | |
|---|---|---|---|---|---|
| | | 350 | 400 | 450 | 500 |
| Promega | αDH5/pBlue | 11 ± 4 | 20 ± 8 | 36 ± 16 | 56 ± 18 |
| | XL1/pBlue | 142 | (stopped) | | |
| Qiagen | αDH5/pBlue | 14 | 21 | 34 | 56 |
| | XL1/pBlue | 7 | 12 | 25 | 39 |
| From Ex. 1 | αDH5/pBlue | 5 | 7 | 10 | 20 |
| | XL1/pBlue | 7 ± 2 | 8 ± 3 | 11 ± 4 | 17 ± 5 |

The purification process supplied by Qiagen is an anion exchange method followed by a silica bonding step and then a wash containing about 80 % ethanol. The purification process supplied by Promega is a silica bonding step followed by a 55 % ethyl alcohol in an 83 mM NaCl and 8 mM TrisHCL pH 7.5 aqueous buffer wash. As can be seen by the sequencing results provided above, the Promega silica based process requires additional purification procedures such as reprecipitation and washes in order to be of suitable purity for automated DNA sequencing analysis. In contrast, DNA prepared in accordance with the present invention is of sufficient purity for use after two washes of a first high alcoholic content and a second lower alcoholic content.

Example 3

In order to demonstrate the effect of variable concentrations of alcohol on the purity of the recovered DNA, experiments were performed using bacterial lysate prepared as described in Example 1. The purification process described in Example 1 was also incorporated into these experiments except that variable amounts of alcohol in water were used in the washes. The purified plasmids were analyzed for absorbance at 260 nm using a ultraviolet spectrophotometer to determine DNA yield. The results shown in Table II indicate total yield in µg/mL of culture using the same culture batch for each purification.

TABLE II

| First Wash Solution | Second Wash Solution | Yield DNA avg µg/mL |
|---|---|---|
| 100% EtOH | 80% EtOH | 1.0 |
| 100% EtOH | 75% EtOH | 1.1 |
| 100% EtOH | 70% EtOH | 0.8 |
| 100% EtOH | 65% EtOH | 0.4 |
| 99% EtOH | 80% EtOH | 1.3 |
| 99% EtOH | 75% EtOH | 1.3 |
| 99% EtOH | 70% EtOH | 0.8 |
| 99% EtOH | 65% EtOH | 0.5 |
| 98% EtOH | 80% EtOH | 1.1 |
| 98% EtOH | 75% EtOH | 1.0 |
| 98% EtOH | 70% EtOH | 0.8 |
| 98% EtOH | 65% EtOH | 0.3 |
| 95% EtOH | 80% EtOH | 1.0 |
| 95% EtOH | 75% EtOH | 1.2 |
| 95% EtOH | 70% EtOH | 0.6 |
| 95% EtOH | 65% EtOH | 0.3 |

The data in Table II illustrate that when a 99 wt % ethyl alcohol first wash solution is combined with a 75 wt % ethyl alcohol second wash solution, yields are generally higher. Furthermore, in addition to the yield data obtained from measuring absorbance at 260, information relating to impurity level can be obtained by observing the protein peak at 280 nm. When 100 % ethyl alcohol is utilized in a first wash, the impurity levels were the highest and relatively unacceptable.

Example 4

Another experiment was performed to analyze the ability of DNA purified using different concentrations of ethyl alcohol to be sequenced using an automated fluorescence cycle sequencer. The samples were obtained and analyzed as described in Examples 1 and 2. The first wash solution was varied as shown in Table III and the second wash solution was 75 % ethyl alcohol in water. Two strains were grown, purified, and sequenced—αDH5 with plasmid pUC18+1.5 KB insert and XL1 with plasmid pB1 +1.5 KB insert. Table III illustrates the results of sequencing a 350 base sequence, a 400 base sequence, a 450 base sequence, and 500 base sequence in terms of the number of sequencing errors observed during the subsequent automated sequencing.

TABLE III

| First Wash EtOH Concentration | Number Sequencing Errors | | | |
|---|---|---|---|---|
| | 350 | 400 | 450 | 500 |
| αDH5 | | | | |
| 98% | 10 | 13 | 26 | 41 |
| 99% | 10 | 16 | 33 | 59 |
| 100% | 21 | 43 | 69 | (stopped) |
| XL1 | | | | |
| 98% | 7 | 13 | 29 | 50 |
| 99% | 8 | 12 | 27 | 45 |
| 100% | 38 | (stopped) | | |

By the above data it can be seen the using a 98 wt % or 99 wt % ethyl alcohol first wash provides good sequencing data without further purification procedures.

Example 5

The following demonstrates the applicability of using other lower alkyl alcohols as wash solutions in accordance with the present invention. Cultures were prepared and silica was treated with the cleared lysate as described in Example 1. The silica was then exposed to various wash procedures. Table IV illustrates the results.

TABLE IV

| First Wash | Second Wash | Yield µg/mL |
|---|---|---|
| 100% EtOH | 100% IPA | 1.5 |
| 100% IPA | 70% EtOH | 0.6 |
| 100% EtOH | MeOH/Acetone | 0.4 |

The above examples are offered to describe certain embodiments of the present invention and are not in any way intended to limit the invention. Those skilled in the art will recognize that many modifications can be practice while remaining within the scope of the above-described invention. For example, the particulate binding support is described as silica. However, it is apparent to those skilled in the art that glass beads, diatomaceous earth, and other similar solid particulates are suitable.

I claim:

1. A method for isolating DNA from a homogeneous mixture of DNA and other material, said method comprising the steps of:
   a) treating silica with said homogeneous mixture in the presence of chaotrope;
   b) washing said treated silica with a first wash solution comprising at least 95 wt % alcohol; and
   c) washing said treated and washed silica with a second wash solution, said second wash solution comprising from about 65% to about 95 wt % alcohol in water, said isolated DNA located on the surface of said silica.

2. The method of claim 1 further comprising the step of eluting said purified DNA from the surface of said silica by treating said washed silica with an aqueous solution after step c).

3. The method of claim 1 wherein steps b) and c) are repeated.

4. The method of claim 1 wherein said alcohol is ethyl alcohol.

5. The method of claim 1 wherein said first wash solution is 95–99 wt % alcohol in water.

6. The method of claim 1 wherein said second wash solution is 70–85 wt % alcohol in water.

7. The method of claim 1 wherein said first wash solution is 99 wt % ethyl alcohol in water and said second wash solution is 75 wt % ethyl alcohol in water.

8. The method of claim 7 further comprising the step of after step a) separating said treated silica by filtration.

9. In a method for isolating DNA from a homogeneous mixture, said method comprising the steps of treating silica with said homogeneous mixture and washing said treated silica with a solution comprising ethanol, said improvement comprising:
   a) treating said silica in said homogeneous mixture in the presence of a chaotrope;
   b) washing said treated silica with a first wash solution comprising greater than 95 wt % alcohol in water; and
   c) washing said washed silica with a second wash solution comprising from about 65% to about 95 wt % alcohol in water.

10. The method of claim 9 wherein said alcohol is ethyl alcohol.

11. The method of claim 9 wherein said first wash solution is 95–99 wt % ethyl alcohol in water.

12. The method of claim 9 wherein said second wash solution is 70–85 wt % ethyl alcohol in water.

13. A method for isolating and purifying DNA from a homogeneous mixture of DNA and other material, said method comprising the step of:
   a) treating silica with said homogeneous mixture in the presence of a chaotropic salt solution;
   b) separating said treated silica from said chaotropic salt solution and mixture;
   c) washing said separated and treated silica with a first wash solution comprising at least 95 wt % ethyl alcohol;
   d) separating said washed silica from said first wash solution;
   e) washing said filtered silica of step d) with a second wash solution, said second wash solution comprising from about 65% to about 95 wt % ethyl alcohol in water, said isolated DNA located on the surface of said silica;
   f) separating said washed silica from said second wash solution; and
   g) eluting said DNA from said silica by washing said washed silica of step f) with an aqueous solution.

14. The method of claim 13 wherein said first wash solution is 95–99 wt % ethyl alcohol in water.

15. The method of claim 13 wherein said second wash solution is about 70–85 wt % ethyl alcohol in water.

16. The method of claim 13 wherein said chaotropic salt solution is concentrated guanidine hydrochloride.

\* \* \* \* \*